United States Patent
Ho et al.

(10) Patent No.: US 11,911,421 B2
(45) Date of Patent: *Feb. 27, 2024

(54) PROBIOTIC COMPOSITION INCLUDING LACTIC ACID BACTERIAL STRAINS AND USE THEREOF

(71) Applicant: GLAC BIOTECH CO., LTD., Tainan (TW)

(72) Inventors: Hsieh-Hsun Ho, Tainan (TW); Wen-Yang Lin, Tainan (TW); Yi-Wei Kuo, Tainan (TW); Yen-Yu Huang, Tainan (TW); Jia-Hung Lin, Tainan (TW)

(73) Assignee: GLAC BIOTECH CO., LTD., Tainan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/455,466

(22) Filed: Nov. 18, 2021

(65) Prior Publication Data

US 2022/0313752 A1    Oct. 6, 2022

(30) Foreign Application Priority Data

Mar. 30, 2021    (TW) .................................. 110111649

(51) Int. Cl.
| | | |
|---|---|---|
| *A61K 35/745* | (2015.01) | |
| *A61K 35/747* | (2015.01) | |
| *A61P 3/10* | (2006.01) | |
| *C12N 1/20* | (2006.01) | |
| *C12R 1/225* | (2006.01) | |

(52) U.S. Cl.
CPC .......... *A61K 35/745* (2013.01); *A61K 35/747* (2013.01); *A61P 3/10* (2018.01); *C12N 1/205* (2021.05); *C12R 2001/225* (2021.05)

(58) Field of Classification Search
None
See application file for complete search history.

(56) References Cited

U.S. PATENT DOCUMENTS 10,286,026 B2 * 5/2019 Israelsen .............. A61K 36/899
10,905,727 B2 * 2/2021 Rottiers ................. C07K 14/55

OTHER PUBLICATIONS

Hsieh, Pei-Shan et al. Lactobacillus salivarius AP-32 and Lactobacillus reuteri GL-104 decrease glycemic levels and attenuate diabetes-mediated liver and kidney injury in db/db mice. BMJ Open Diab Res Care 2020. pp. 1-9. (Year: 2020).*

* cited by examiner

*Primary Examiner* — Nghi V Nguyen
(74) *Attorney, Agent, or Firm* — Nixon & Vanderhye PC

(57) ABSTRACT

Disclosed herein is a probiotic composition that includes *Lactobacillus salivarius* subsp. *salicinius* AP-32, *Lactobacillus johnsonii* MH-68, and *Bifidobacterium animalis* subsp. *lactis* CP-9, which are deposited at the China Center for Type Culture Collection (CCTCC) respectively under accession numbers CCTCC M 2011127, CCTCC M 2011128, and CCTCC M 2014588. A number ratio of *Lactobacillus salivarius* subsp. *salicinius* AP-32, *Lactobacillus johnsonii* MH-68, and *Bifidobacterium animalis* subsp. *lactis* CP-9 ranges from 1:0.1:0.1 to 1:1:8. Also disclosed herein is use of the probiotic composition for alleviating type 1 diabetes mellitus (T1DM).

4 Claims, No Drawings

PROBIOTIC COMPOSITION INCLUDING LACTIC ACID BACTERIAL STRAINS AND USE THEREOF

CROSS-REFERENCE TO RELATED APPLICATION

This application claims priority of Taiwanese Invention Patent Application No. 110111649, filed on Mar. 30, 2021.

FIELD

The present disclosure relates to a probiotic composition including three lactic acid bacterial strains. The present disclosure also relates to a method for alleviating type 1 diabetes mellitus (T1DM) using the probiotic composition.

BACKGROUND

Diabetes mellitus (DM) is a family of disorders characterized by chronic hyperglycemia. The two main types of diabetes mellitus are type 1 diabetes mellitus (T1DM) and type 2 diabetes mellitus (T2DM). T1DM (also known as insulin-dependent diabetes mellitus (IDDM) or juvenile diabetes) is an autoimmune disease that permanently destroys insulin-producing pancreatic p cells and abolishes the production of endogenous insulin. T1DM may cause diabetic ketoacidosis and lead to nonketotic hyperosmolar coma, heart diseases, stroke, kidney failure, foot ulcers, etc.

Several treatment strategies, such as diet and nutrition management, exercise, use of hypoglycemic agents, insulin replacement therapy (i.e., injection of exogenous insulin), pancreas transplantation, and islet cell transplantation, have been taken to combat T1DM. However, these treatment strategies might not be able to achieve the desired therapeutic effect and might also cause severe side effects.

Probiotics are resident normal flora of the intestinal tract and believed to play important roles in regulating proper intestinal immunity and digestion by balancing intestinal microflora. These beneficial microorganisms are widely used as live microbial dietary supplements and can help restoring intestinal microfloral balance. Many species of lactic acid bacteria (LAB) are conferred with the generally recognized as safe (GRAS) status, and are widely used as probiotics.

Common LAB include *Lactobacillus* spp., *Lactococcus* spp., *Pediccoccus* spp., *Streptococcus* spp., *Enterococcus* spp., *Bifidobacterium* spp., *Bacillus* spp., *Leuconostoc* spp., etc. LAB have been shown to be capable of inhibiting the growth of pathogenic bacteria in the gastrointestinal tract and alleviating lactose intolerance, and to have anti-cancer, anti-bacterial, anti-fatigue, and blood pressure lowering effects.

Previous studies demonstrated that certain strains of LAB are effective in ameliorating T2DM. For example, it has been reported in Hsieh P. S. et al. (2020), *BMJ Open Diabetes Res. Care*, doi: 10.1136/bmjdrc-2019-001028 that C57BL/6J-db/db diabetic mice administered with *Lactobacillus salivarius* AP-32, *Lactobacillus reuteri* GL-104, or a combination thereof showed a significant decrease in fasting blood glucose levels, and improvement in glucose tolerance and blood lipid profiles.

In spite of the aforesaid, there is still a need to develop a new strategy that can be utilized in the alleviation of T1DM.

SUMMARY

Accordingly, in a first aspect, the present disclosure provides a probiotic composition which can alleviate at least one of the drawbacks of the prior art.

The probiotic composition includes *Lactobacillus salivarius* subsp. *salicinius* AP-32, *Lactobacillus johnsonii* MH-68, and *Bifidobacterium animalis* subsp. *lactis* CP-9, which are deposited at the China Center for Type Culture Collection (CCTCC) respectively under accession numbers CCTCC M 2011127, CCTCC M 2011128, and CCTCC M 2014588. A number ratio of *Lactobacillus salivarius* subsp. *salicinius* AP-32, *Lactobacillus johnsonii* MH-68, and *Bifidobacterium animalis* subsp. *lactis* CP-9 ranges from 1:0.1:0.1 to 1:1:8.

In a second aspect, the present disclosure provides a method for alleviating type 1 diabetes mellitus (T1DM), which can alleviate at least one of the drawbacks of the prior art, and which includes administering to a subject in need thereof the aforesaid probiotic composition.

DETAILED DESCRIPTION

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

By virtue of research, the applicant surprisingly found that a mixture of *Lactobacillus salivarius* subsp. *salicinius* AP-32, *Lactobacillus johnsonii* MH-68, and *Bifidobacterium animalis* subsp. *lactis* CP-9 in a particular ratio is capable of reducing blood glucose and hemoglobin A1c (HbA1c) levels, and hence expected such mixture to be effective in alleviating type 1 diabetes mellitus (T1DM).

Therefore, the present disclosure provides a probiotic composition, which includes *Lactobacillus salivarius* subsp. *salicinius* AP-32, *Lactobacillus johnsonii* MH-68, and *Bifidobacterium animalis* subsp. lactic CP-9, which are deposited at the China Center for Type Culture Collection (CCTCC) respectively under accession numbers CCTCC M 2011127, CCTCC M 2011128, and CCTCC M 2014588. A number ratio of *Lactobacillus salivarius* subsp. *salicinius* AP-32, *Lactobacillus johnsonii* MH-68, and *Bifidobacterium animalis* subsp. *lactis* CP-9 ranges from 1:0.1:0.1 to 1:1:8.

In certain embodiments, the number ratio of *Lactobacillus salivarius* subsp. *salicinius* AP-32, *Lactobacillus johnsonii* MH-68, and *Bifidobacterium animalis* subsp. *lactis* CP-9 ranges from 1:0.5:0.5 to 1:1:2. In an exemplary embodiment, the number ratio of *Lactobacillus salivarius* subsp. *salicinius* AP-32, *Lactobacillus johnsonii* MH-68, and *Bifidobacterium animalis* subsp. *lactis* CP-9 is 1:1:1.

According to the present disclosure, *Lactobacillus salivarius* subsp. *salicinius* AP-32, *Lactobacillus johnsonii* MH-68, and *Bifidobacterium animalis* subsp. *lactis* CP-9 may be live cells or dead cells, concentrated or non-concentrated, a liquid, a paste, a semi-solid, or a solid (e.g., a pellet, a granule, or a powder), and may be heat-inactivated, frozen, dried, or freeze-dried (e.g., may be in freeze-dried form or spray/fluid bed dried form).

In certain embodiments, the probiotic composition of the present disclosure may be formulated as a food product using a standard technique well known to one of ordinary skill in the art. For instance, the aforesaid probiotic composition may be directly added to an edible material, or may be utilized for preparing an intermediate composition (e.g., a food additive or a premix) suitable to be subsequently added to the edible material.

As used herein, the term "food product" refers to any article or substance that can be ingested by a subject into the body thereof. Examples of the food product may include, but are not limited to, fluid milk products (e.g., milk and concentrated milk), fermented milk (e.g., yogurt, sour milk, and frozen yogurt), milk powder, ice cream, cream cheese, dry cheese, soybean milk, fermented soybean milk, vegetable fruit juice, fruit juice, sport drinks, jelly, cookies, energy bars, health foods, animal feeds, and dietary supplements.

In certain embodiments, the probiotic composition of the present disclosure may be prepared in the form of a pharmaceutical composition. The pharmaceutical composition may be formulated into a suitable dosage form for oral or parenteral administration using technology well known to those skilled in the art.

According to the present disclosure, the suitable dosage form for oral administration includes, but is not limited to, sterile powders, tablets, troches, lozenges, pellets, capsules, dispersible powders or granules, solutions, suspensions, emulsions, syrup, elixir, slurry, and the like.

The pharmaceutical composition according to the present disclosure may be administered via one of the following parenteral routes: intraperitoneal injection, intrapleural injection, intramuscular injection, intravenous injection, intraarterial injection, intraarticular injection, intrasynovial injection, intrathecal injection, intracranial injection, intraepidermal injection, subcutaneous injection, intradermal injection, intralesional injection, and sublingual administration.

According to the present disclosure, the pharmaceutical composition may further include a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of the aforesaid agents are within the expertise and routine skills of those skilled in the art.

The present disclosure also provides a method for alleviating T1DM, which includes administering to a subject in need thereof the aforesaid probiotic composition.

As used herein, the term "alleviating" or "alleviation" refers to at least partially reducing, ameliorating, relieving, controlling, treating or eliminating one or more clinical signs of a disease or disorder; and lowering, delaying, stopping or reversing the progression of severity regarding the condition or symptom being treated and preventing or decreasing the likelihood or probability thereof.

As used herein, the term "administering" or "administration" means introducing, providing or delivering a predetermined active ingredient to a subject by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human. In an exemplary embodiment, the subject is a female human.

The dose and frequency of administration of the probiotic composition of the present disclosure may vary depending on the following factors: the severity of the illness or disorder to be treated, routes of administration, and age, physical condition and response of the subject to be treated. In general, the probiotic composition may be administered in a single dose or in several doses.

The disclosure will be further described by way of the following examples. However, it should be understood that the following examples are solely intended for the purpose of illustration and should not be construed as limiting the disclosure in practice.

EXAMPLES

General Experimental Materials

1. Lactic Acid Bacterial (LAB) Strains

*Lactobacillus salivarius* subsp. *salicinius* AP-32 (which is disclosed in TW 1384990 B and CN 102835666 B), *Lactobacillus johnsonii* MH-68 (which is disclosed in TW 1384990 B and CN 102835666 B), and *Bifidobacterium animalis* subsp. *lactis* CP-9 (which is disclosed in TW 1572713 B and CN 105985918 B) have been deposited at the Bioresource Collection and Research Center (BCRC) of the Food Industry Research and Development Institute (FIRDI) (No. 331, Shih-Pin Rd., Hsinchu City 300, Taiwan), and have also been deposited at the China Center for Type Culture Collection (CCTCC) of Wuhan University, the College of Life Sciences (No. 299, Bayi Rd., Wuchang District, Wuhan City, Hubei Province, 430072, China) in accordance with the Budapest Treaty.

The relevant information regarding each of the LAB strains (including accession number and date of deposit) is listed in Table 1 below.

TABLE 1

| LAB strains | Accession number | Date of deposit |
|---|---|---|
| Lactobacillus salivarius subsp. salicinius AP-32 | BCRC 910437 CCTCC M 2011127 | Jul. 30, 2009 Apr. 10, 2011 |
| Lactobacillus johnsonii MH-68 | BCRC 910438 CCTCC M 2011128 | Jul. 30, 2009 Apr. 10, 2011 |
| Bifidobacterium animalis subsp. lactis CP-9 | BCRC 910645 CCTCC M 2014588 | Aug. 21, 2014 Nov. 24, 2014 |

General Procedures:
1. Statistical Analysis

All the experiments described below were performed in triplicate. The experimental data are expressed as mean ± standard deviation (SD). All the data were analyzed using two-tailed Mann-Whitney U test, so as to evaluate the differences between the groups. Statistical significance is indicated by $p<0.05$.

Example 1. Preparation of Probiotic Composition of Present Disclosure

A respective one of *Lactobacillus salivarius* subsp. *salicinius* AP-32, *Lactobacillus johnsonii* MH-68, and *Bifidobacterium animalis* subsp. *lactis* CP-9 was inoculated in a MRS broth (Difco) supplemented with 0.05% (w/w) cysteine, and was then cultivated in an incubator (37° C.) for 24 hours to obtain a respective inoculum. Thereafter, the inoculum of the respective one of *Lactobacillus salivarius* subsp. *salicinius* AP-32 and *Lactobacillus johnsoii* MH-68 was inoculated in an amount of 2% (v/v) (bacterial number: $10^8$ CFU) into 5 mL of a MRS medium supplemented with 60 mg/mL glucose, and the inoculum of *Bifidobacterium animalis* subsp. *lactis* CP-9 was inoculated in an amount of 2% (v/v) (bacterial number: $10^8$ CFU) into 5 mL of a MRS medium supplemented with 60 mg/mL glucose and 0.05% (w/w) cysteine, followed by cultivation in an incubator (37° C.) for 20 hours.

After centrifugation at 3,000 rpm and 4° C. for 10 minutes, the resultant cell pellet was collected, and was washed with 0.1 M phosphate-buffered saline (PBS), followed by suspending in PBS, so as to obtain a bacterial suspension. The bacterial suspensions of *Lactobacillus salivarius* subsp. *salicinius* AP-32, *Lactobacillus johnsonii* MH-68, and *Bifidobacterium animalis* subsp. *lactis* CP-9 were mixed in a number ratio of 1:1:1, so as to obtain a LAB mixture suspension having a bacterial concentration of $10^{10}$ CFU/mL. The resultant LAB mixture suspension was subjected to a freeze-drying process, and the probiotic composition thus obtained was used for the following example.

Example 2. Evaluation for the Effect of Probiotic Composition According to this Disclosure on Alleviating Type 1 Diabetes Mellitus (T1DM)

A. Test Subjects 56 test subjects (including 32 male subjects and 24 female subjects) participating in the following tests were enrolled from China Medical University Hospital, Taiwan. The tests were approved by the Research Ethics Committee of China Medical University Hospital and were conducted according to the principles of the Declaration of Helsinki. In addition, written informed consent was obtained from each of the test subjects.

These test subjects (at the age between 6 and 18 years) were diagnosed with T1DM, and were selected and enrolled according to the inclusion and exclusion criteria as outlined in Table 2.

TABLE 2

| Inclusion criteria | 1 | The candidate was diagnosed with ketoacidosis. |
|---|---|---|
| | 2 | The candidate had insulin autoantibodies (IAAs). |
| | 3 | The candidate had an insulin-deficiency disorder. |
| Exclusion criteria | 1 | The candidate had a heart, kidney, or liver disease. |
| | 2 | The candidate had an immunodeficiency or hypoimmunity disorder. |
| | 3 | The candidate took probiotic supplements for more than 1 month before the test. |
| | 4 | The candidate had an allergic reaction to probiotic supplements. |

B. Administration of Probiotic Composition and Preparation of Blood Samples

The 56 test subjects were randomly divided into an experimental group (including 13 male subjects and 14 female subjects) and a control group (including 19 male subjects and 10 female subjects). The respective test subject of the experimental group was orally administered with 0.5 g of the probiotic composition obtained in Example 1, and the respective test subject of the control group was orally administered with 0.5 g of a mixture containing maltitol, indigestible maltodextrin, and bromelin. Each test subject was administered twice daily for a 6-month treatment period. In addition, each test subject received an insulin injection therapy during the 6-month treatment period.

Prior to the start of the treatment (i.e., at Month 0), at the end of Month 6 after starting oral administration of the probiotic composition of the present disclosure, and at the end of the three months after stopping the treatment, the respective test subject was subjected to fasting for at least 8 hours overnight. Thereafter, a blood sample was collected from the vein of each test subject through puncture.

C. Determination of Blood Glucose and Hemoglobin A1c (HbA1c) Levels

The blood sample of each test subject obtained in section B of this example at each of the time points was subjected to determination of blood glucose level using an Optium Xceed blood glucose meter (Abbott Diabetes Care Inc.) in accordance with the manufacturer's instructions.

The relative blood glucose level of each test subject in a respective one of the experimental group and control group was calculated by substituting the thus determined blood glucose level into the following Equation (I):

$$A=(B/C)\times100 \qquad (I)$$

where A=relative blood glucose level (%)
B=blood glucose level determined at the end of the 6-month treatment period or at the end of three months after stopping the treatment
C=blood glucose level determined at Month 0

In addition, the blood sample of each test subject obtained in section B of this example at each of the time points was subjected to determination of HbA1c level using a HbA1c high performance liquid chromatography (HPLC) assay kit (Eagle Biosciences, Cat. No. A1C31-H100) and a PerkinElmer Series 200 HPLC system in accordance with the manufacturer's instructions.

The relative HbA1c level of each test subject in a respective one of the experimental group and control group was calculated by substituting the thus determined HbA1c level into the following Equation (II):

$$D=(E/F)\times100 \qquad (II)$$

where D=relative HbA1c level (%)
E=HbA1c level determined at the end of the 6-month treatment period
F=HbA1c level determined at Month 0

The data thus obtained were analyzed according to the method described in section 1 of "General Procedures".

Table 3 shows the relative blood glucose level and the relative HbA1c level in each group after the 6-month treatment period. As shown in Table 3, the relative blood glucose level and the relative HbA1c level determined in the experimental group were significantly lower than those determined in the control group.

TABLE 3

| Group | Relative blood glucose level (%) | Relative HbA1c level (%) |
|---|---|---|
| Control group | 101.5 | 100.1 |
| Experimental group | 87.5*** | 91.8*** |

***when compared to the control group, p < 0.005.

Table 4 shows the relative blood glucose level in each group at the end of the three months after stopping the treatment. As shown in Table 4, the relative blood glucose level determined in the experimental group was lower than that determined in the control group. In particular, the relative blood glucose level determined in the female test subjects of the experimental group was significantly lower than that determined in the female test subjects in the control group, and was apparently lower than that determined in the male test subjects in the control group.

TABLE 4

| Group | | Relative blood glucose level (%) |
|---|---|---|
| Control group | Male test subjects | 102.1 ± 12.1 |
| | Female test subjects | 104.2 ± 21.2 |
| | All test subjects | 103.5 ± 18.3 |
| Experimental group | Male test subjects | 90.2 ± 13.3* |
| | Female test subjects | 87.8 ± 15.9* |
| | All test subjects | 89.0 ± 14.4 |

*When compared to the test subjects of the same sex in the control group, $p < 0.05$.

Summarizing the above test results, it is clear that the probiotic composition of present disclosure is capable of effectively reducing the blood glucose and HbA1c levels, and hence can alleviate T1DM.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for alleviating type 1 diabetes mellitus (T1DM), comprising administering to a subject in need thereof a probiotic composition,
   wherein the probiotic composition comprises *Lactobacillus salivarius* subsp. *salicinius* AP-32, *Lactobacillus johnsonii* MH-68, and *Bifidobacterium animalis* subsp. *lactis* CP-9, which are deposited at the China Center for Type Culture Collection (CCTCC) respectively under accession numbers CCTCC M 2011127, CCTCC M 2011128, and CCTCC M 2014588,
   wherein a number ratio of *Lactobacillus salivarius* subsp. *salicinius* AP-32, *Lactobacillus johnsonii* MH-68, and *Bifidobacterium animalis* subsp. *lactis* CP-9 ranges from 1:0.1:0.1 to 1:1:8, and
   wherein the probiotic composition is in a dosage form for oral administration, and has a bacterial concentration of $10^{10}$ CFU/mL, and
   wherein the subject is administered with the probiotic composition twice daily for a 6-month treatment period.

2. The method as claimed in claim 1, wherein the number ratio of *Lactobacillus salivarius* subsp. *salicinius* AP-32, *Lactobacillus johnsonii* MH-68, and *Bifidobacterium animalis* subsp. *lactis* CP-9 is 1:1:1.

3. The method as claimed in claim 1, wherein the probiotic composition is formulated as a food product.

4. The method as claimed in claim 1, wherein the probiotic composition is formulated as a pharmaceutical composition.

* * * * *